(12) United States Patent
Strohallen et al.

(10) Patent No.: US 8,723,668 B1
(45) Date of Patent: May 13, 2014

(54) SYSTEM AND METHOD FOR CONTROLLING AT LEAST ONE DEVICE

(76) Inventors: Gene Michael Strohallen, North Manchester, IN (US); Thomas P. Warner, Rochester Hills, MI (US)

( * ) Notice: Subject to any disclaimer, the term of this patent is extended or adjusted under 35 U.S.C. 154(b) by 400 days.

(21) Appl. No.: 13/317,395

(22) Filed: Oct. 17, 2011

Related U.S. Application Data

(60) Provisional application No. 61/455,109, filed on Nov. 14, 2010.

(51) Int. Cl.
G08C 19/00 (2006.01)

(52) U.S. Cl.
USPC ..... 340/539.12; 340/7.1; 340/7.32; 340/12.5; 340/539.1; 433/96; 433/101; 606/34

(58) Field of Classification Search
USPC ......... 340/501, 531, 539.1, 539.12, 7.1, 7.32, 340/12.5, 13.24, 13.25; 433/77, 98, 101; 606/34, 169, 185
See application file for complete search history.

(56) References Cited

U.S. PATENT DOCUMENTS

| | | |
|---|---|---|
| 4,114,275 A | 9/1978 | Jones et al. |
| 4,156,187 A | 5/1979 | Brumbach et al. |
| 4,171,572 A | 10/1979 | Nash |
| 4,180,812 A | 12/1979 | Beier et al. |
| 4,241,331 A | 12/1980 | Neumayr et al. |
| 4,305,126 A | 12/1981 | Beier et al. |
| 4,509,526 A | 4/1985 | Barnes et al. |
| 4,571,681 A | 2/1986 | Beier et al. |
| 5,030,956 A | 7/1991 | Murphy |
| 5,223,816 A | 6/1993 | Levinson et al. |
| 5,268,624 A | 12/1993 | Zanger |
| 5,355,804 A | 10/1994 | Garcia et al. |
| 5,408,284 A | 4/1995 | Berger et al. |
| 5,422,521 A | 6/1995 | Neer et al. |
| 5,838,131 A | 11/1998 | Telymonde |
| 5,931,669 A | 8/1999 | Fornoff et al. |
| 5,934,904 A | 8/1999 | Elrod et al. |
| 5,970,457 A | 10/1999 | Brant et al. |
| 6,017,354 A | 1/2000 | Culp et al. |
| 6,074,388 A | 6/2000 | Tockweiler et al. |
| 6,131,130 A | 10/2000 | Van Ryzin |
| 6,249,673 B1 | 6/2001 | Tsui |
| 6,703,941 B1 | 3/2004 | Blaker |
| 6,985,749 B2 | 1/2006 | Bannasch et al. |
| 6,993,314 B2 | 1/2006 | Lim et al. |
| 7,422,432 B2 | 9/2008 | Warner |
| 7,625,208 B2 | 12/2009 | Warner |
| 7,659,833 B2 | 2/2010 | Warner et al. |

(Continued)

Primary Examiner — Brent Swarthout
(74) Attorney, Agent, or Firm — Buckert Patent & Trademark Law Firm, P.C.; John F. Buckert

(57) ABSTRACT

A system and a method for remotely controlling at least one device based on operation of a foot pedal apparatus are provided. The system includes a device selection module (DSM) configured to transmit a first modulated RF signal at a first RF frequency having a communication linking command and a first RF frequency identifier. The first RF frequency identifier indicates a second RF frequency different than the first RF frequency. The system further includes a device control module (DCM) configured to receive the first modulated RF signal at the first RF frequency and to compare the communication linking command to a predetermined communication linking command. If the communication linking command corresponds to the predetermined communication linking command then the DCM selects the second RF frequency based on the first RF frequency identifier for subsequent RF signal reception.

18 Claims, 12 Drawing Sheets

(56) References Cited

U.S. PATENT DOCUMENTS

| | | |
|---|---|---|
| 7,675,430 B2 | 3/2010 | Warner et al. |
| 2002/0126036 A1 | 9/2002 | Flaherty et al. |
| 2004/0143222 A1 | 7/2004 | Spinello |
| 2005/0130097 A1 | 6/2005 | Warner |
| 2005/0130098 A1 | 6/2005 | Warner |
| 2005/0251228 A1 | 11/2005 | Hamel |
| 2007/0030166 A1 | 2/2007 | Warner et al. |
| 2007/0031781 A1 | 2/2007 | Warner et al. |
| 2007/0254261 A1* | 11/2007 | Rosenblood et al. ........... 433/98 |
| 2008/0140158 A1 | 6/2008 | Hamel et al. |
| 2010/0130964 A1* | 5/2010 | Ware et al. ........................ 606/1 |
| 2012/0005296 A1* | 1/2012 | Lint et al. ....................... 709/208 |
| 2013/0096599 A1* | 4/2013 | Colton et al. .................. 606/186 |

\* cited by examiner

LOOKUP TABLE IN DSM MEMORY DEVICE — 70

| OFFICE ADDRESS | ROOM ADDRESS | RF FREQUENCY IDENTIFIER | RF FREQUENCY VALUE |
|---|---|---|---|
| 0000 | 0000 | 0000 | 900 MHz |
| 0001 | 0001 | 0001 | 905 MHz |
| 0010 | 0010 | 0010 | 910 MHz |

*FIG. 11*

LOOKUP TABLE IN FPMM MEMORY DEVICE — 206

| OFFICE ADDRESS | ROOM ADDRESS | RF FREQUENCY IDENTIFIER | RF FREQUENCY VALUE |
|---|---|---|---|
|  |  |  |  |
| 0001 | 0001 | 0001 | 905 MHz |
| 0010 | 0010 | 0010 | 910 MHz |

*FIG. 12*

LOOKUP TABLE IN DCM MEMORY DEVICE — 130

| RF FREQUENCY IDENTIFIER | RF FREQUENCY VALUE |
|---|---|
| 0000 | 900 MHz |
| 0001 | 905 MHz |
| 0010 | 910 MHz |

*FIG. 13*

SYSTEM AND METHOD FOR CONTROLLING AT LEAST ONE DEVICE

CROSS REFERENCE TO RELATED APPLICATIONS

This application claims priority to U.S. Provisional Patent Application Ser. No. 61/455,109 filed Nov. 14, 2010, which is incorporated by reference herein in its entirety.

BACKGROUND

A foot pedal has been utilized to control a device operably coupled to the foot pedal.

SUMMARY

A system for remotely controlling at least a first device based on operation of a foot pedal apparatus in accordance with an exemplary embodiment is provided. The foot pedal apparatus has a movable member. The system includes a device selection module configured to transmit a first modulated RF signal at a first RF frequency having a communication linking command and a first RF frequency identifier. The first RF frequency identifier indicates a second RF frequency different than the first RF frequency. The system further includes a device control module configured to receive the first modulated RF signal at the first RF frequency and to compare the communication linking command to a predetermined communication linking command. If the communication linking command corresponds to the predetermined communication linking command then the device control module selects the second RF frequency based on the first RF frequency identifier for subsequent RF signal reception. The system further includes a foot pedal monitoring module configured to transmit a second modulated RF signal at the second RF frequency in response to at least partial displacement of the moveable member of the foot pedal apparatus from a first operational position. The device control module is further configured to receive the second modulated RF signal at the second RF frequency and to control operation of the first device in response to the second modulated RF signal.

A method for remotely controlling at least a first device based on operation of a foot pedal apparatus having a movable member in accordance with another exemplary embodiment is provided. The method includes transmitting a first modulated RF signal at a first RF frequency having a communication linking command and a first RF frequency identifier utilizing a device selection module. The first RF frequency identifier indicates a second RF frequency different than the first RF frequency. The method further includes receiving the first modulated RF signal at the first RF frequency at a device control module and comparing the communication linking command to a predetermined communication linking command utilizing the device control module. The method further includes determining if the communication linking command corresponds to the predetermined communication linking command and then selecting the second RF frequency based on the first RF frequency identifier utilizing the device control module for subsequent RF signal reception by the device control module. The method further includes transmitting a second modulated RF signal at the second RF frequency from a foot pedal monitoring module in response to at least partial displacement of the moveable member of the foot pedal apparatus from a first operational position. The method further includes receiving the second modulated RF signal at the second RF frequency at the device control module and controlling operation of the first device in response to the second modulated RF signal utilizing the device control module.

BRIEF DESCRIPTION OF THE DRAWINGS

FIG. 11 is a schematic of a lookup table utilized by the device selection module of FIG. 2;

FIG. 12 is a schematic of a lookup table utilized by the foot pedal monitoring module of FIG. 4;

FIG. 13 is a schematic of a lookup table utilized by the device control module of FIG. 3;

DETAILED DESCRIPTION OF EXEMPLARY EMBODIMENTS

Figure 1:
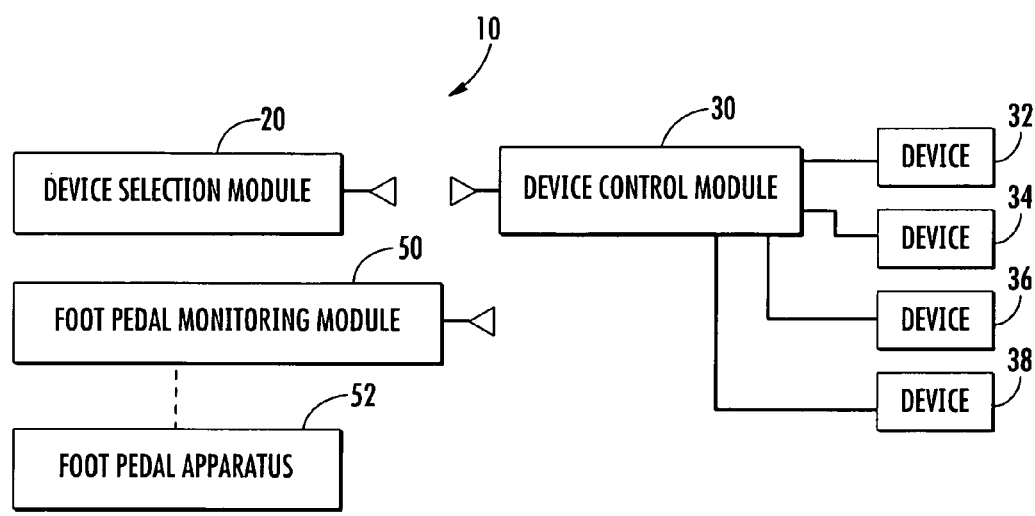
FIG. 1 is a block diagram of a system for remotely controlling devices having a device selection module, a device control module, a foot pedal monitoring module, and a foot pedal apparatus in accordance with an exemplary embodiment.
Figure 4:
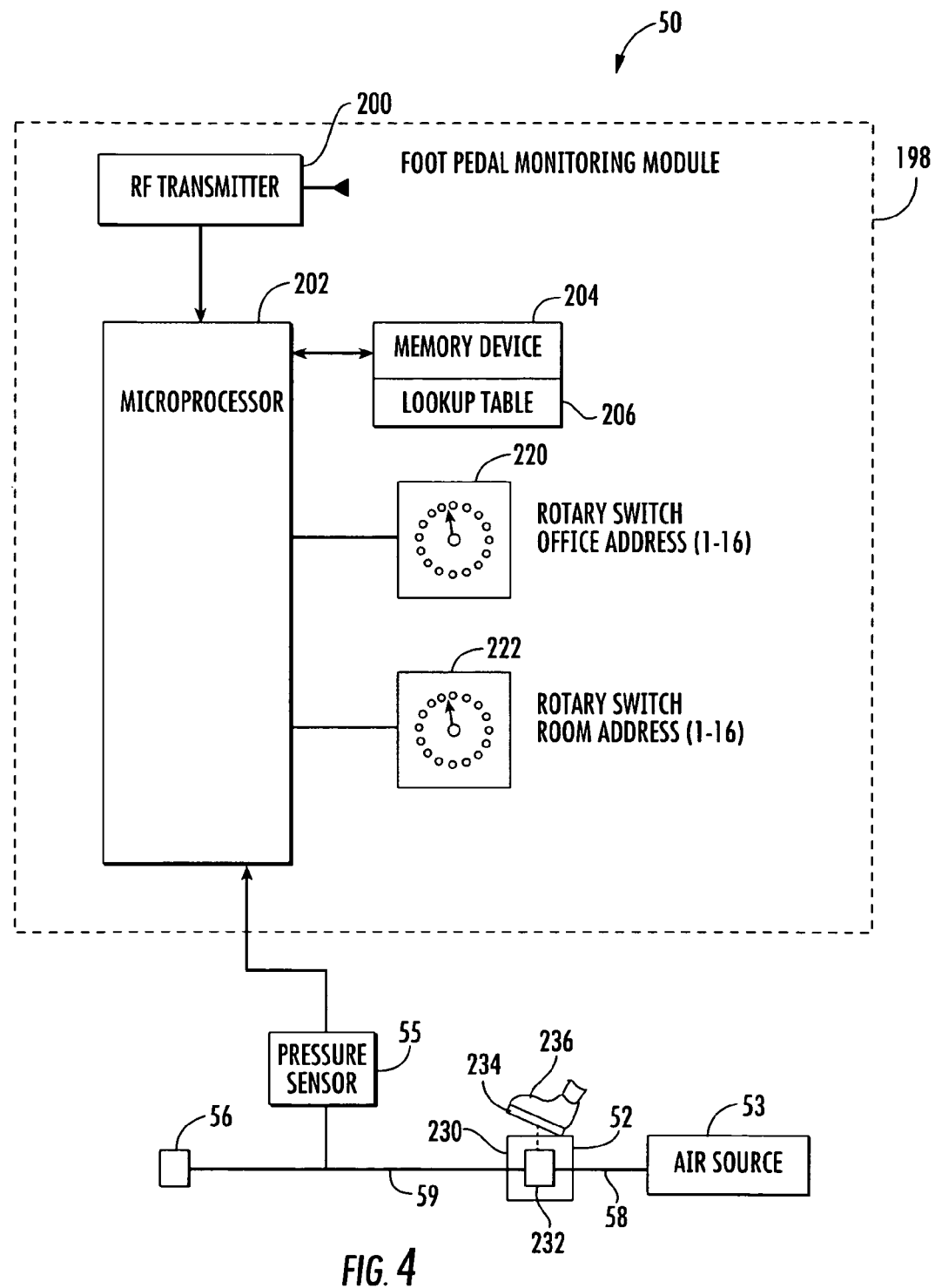
FIG. 4 is a block diagram of the foot pedal monitoring module and other components utilized in the system of FIG. 1.

Referring to FIGS. 1 and 4, a system 10 for remotely controlling devices 32, 34, 36, 38 in accordance with an exemplary embodiment is illustrated. The system 10 includes a device selection module (DSM) 20, a device control module (DCM) 30, a foot pedal monitoring module (FPMM) 50, a foot pedal apparatus 52, an air source 53, a pressure sensor 55, a valve 56, and pneumatic tubes 58, 59.

Figure 2:
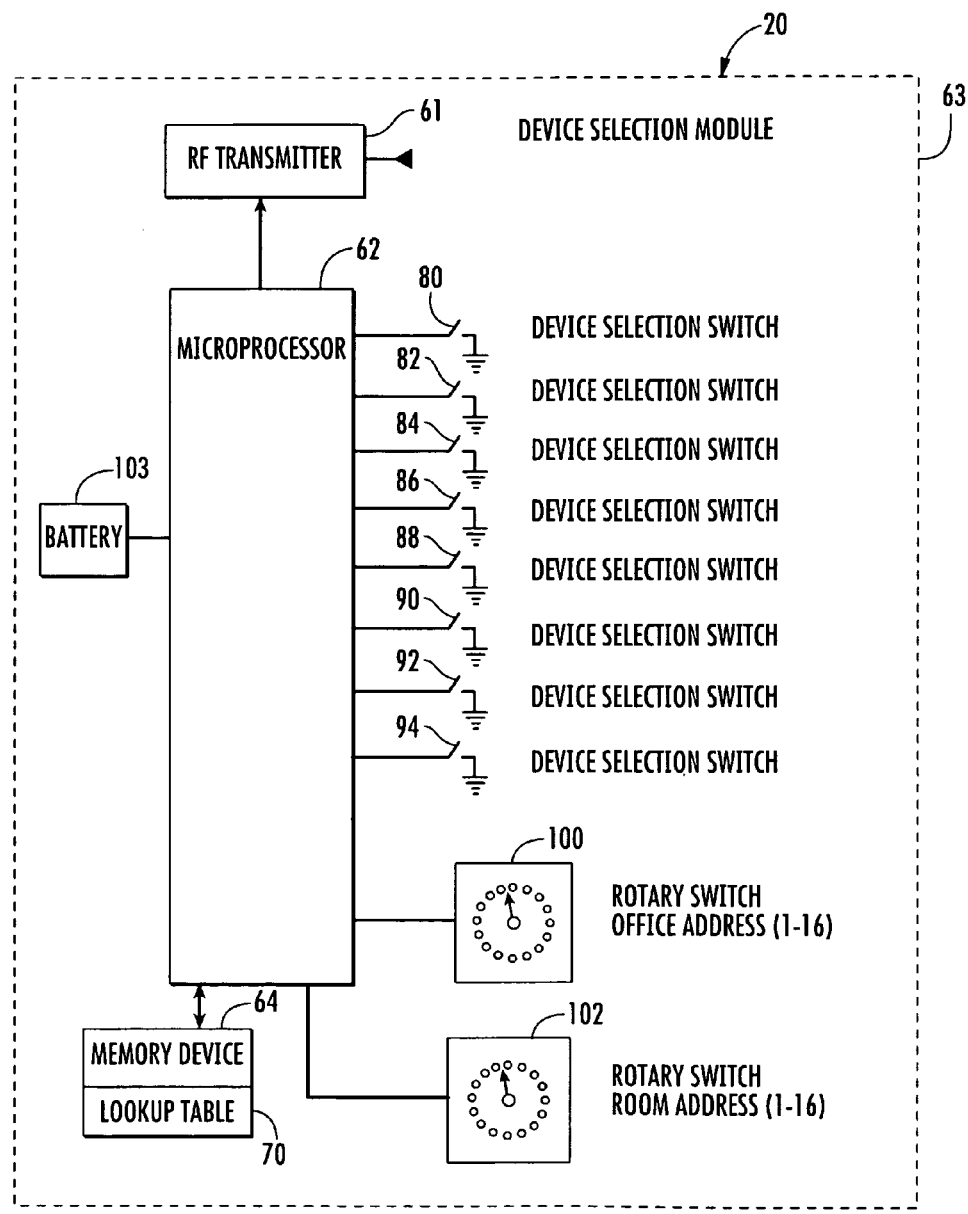
FIG. 2 is a block diagram of the device selection module utilized in the system of FIG. 1.

Referring to FIGS. 1 and 2, the DSM 20 is provided to establish a communication link with the DCM 30 and to allow a user to select one of a plurality of device selection switches that is associated with a respective device operably coupled to the DCM 30. The DSM 20 includes an RF transmitter 61, a microprocessor 62, a hand-held housing 63, a memory device 64 having a lookup table 70, device selection switches 80, 82, 84, 86, 88, 90, 92, 94, rotary switches 100, 102, and a battery 103.

The hand-held housing 63 holds the RF transmitter 61, the microprocessor 62, the memory device 64, and the battery 103 therein. The device selection switches 80, 82, 84, 86, 88, 90, 92, 94, and the rotary switches 100, 102 extend at least partially through the hand-held housing 63 and are readily accessible by a user.

Referring to FIGS. 1, 2 and 11, the microprocessor 62 utilizes the lookup table 70 to determine an RF frequency to utilize when communicating with the DCM 30. In one exemplary embodiment, the lookup table 70 has the following fields: (i) office address, (ii) room address, (iii) RF frequency identifier, and (iv) RF frequency value. In particular, the microprocessor 62 accesses a record 302 in the table 70 to determine an initial RF frequency to use for initially communicating with the DCM 30. Thereafter, the microprocessor 62 utilizes the office address and room address indicated by the rotary switches 100, 102, respectively, to select one of the records 304, 306 to determine a jump-to frequency indicated by an RF frequency value in the selected record for subsequent long-term communication with the DCM 30, as will be discussed in greater detail below. Although the exemplary lookup table 70 is illustrated with three records for purposes of simplicity, in an alternative embodiment, the lookup table 70 could have a plurality of additional records each having a distinct office address, room address, RF frequency identifier, and RF frequency value.

Figure 7:
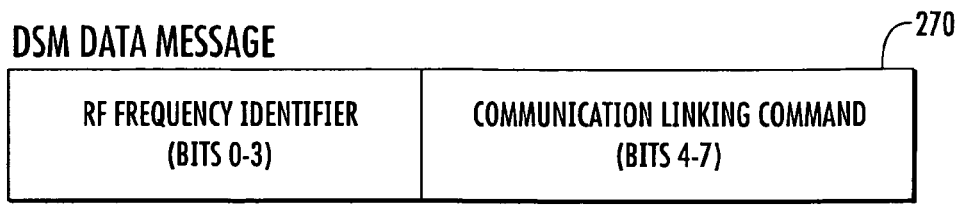
FIG. 7 is a schematic of a data message in a modulated RF signal transmitted by the device selection module of FIG. 2.

Referring to FIGS. 2, 7 and 11, the microprocessor 62 is operably coupled to the RF transmitter 61, the memory device 64, the device selection switches 80-94, and the rotary switches 100, 102. The operational position of the rotary switch 100 indicates an office address (0-15) associated with the DSM 20. The operational position of the rotary switch 102 indicates a room address (0-15) associated with the DSM 20. When a user depresses one of the device selection switches 80-94 in a closed operational position for a predetermined amount of time indicating that a communication linking operation with the DCM 30 is desired, the microprocessor 62 accesses the record 302 in the table 70 in the memory device 64 to determine an initial RF frequency (e.g., 900 MHz) to utilize for initially communicating with the DCM 30. The microprocessor 62 also accesses another record in the table 70 to determine a jump-to RF frequency for subsequent long-term communication with the DCM 30 based on the operational positions of the rotary switches 100, 102. For example, if an operational position of the rotary switch 100 indicates an office address "0001" and a room address "0001", the microprocessor 62 accesses the record 304 having the office address value "0001" and the room address value "0001" to determine both the RF frequency identifier "0001", and the RF frequency value of 905 MHz representing the jump-to RF frequency. Further, the microprocessor 62 generates a control signal to induce the RF transmitter 61 to transmit a modulated RF signal at the initial RF frequency (e.g., 900 MHz) having a data message 270 therein to be received by the DCM 30. The data message 270 has: (i) the RF frequency identifier (e.g., "0001") at bit positions 0-3 indicating the jump-to frequency (e.g., 905 MHz) for subsequent long-term communication with the DCM 30, and (ii) a communication linking command (e.g., "1111") at bit positions 4-7 indicating that a communication linking operation with the DCM 30 is desired.

Figure 3:
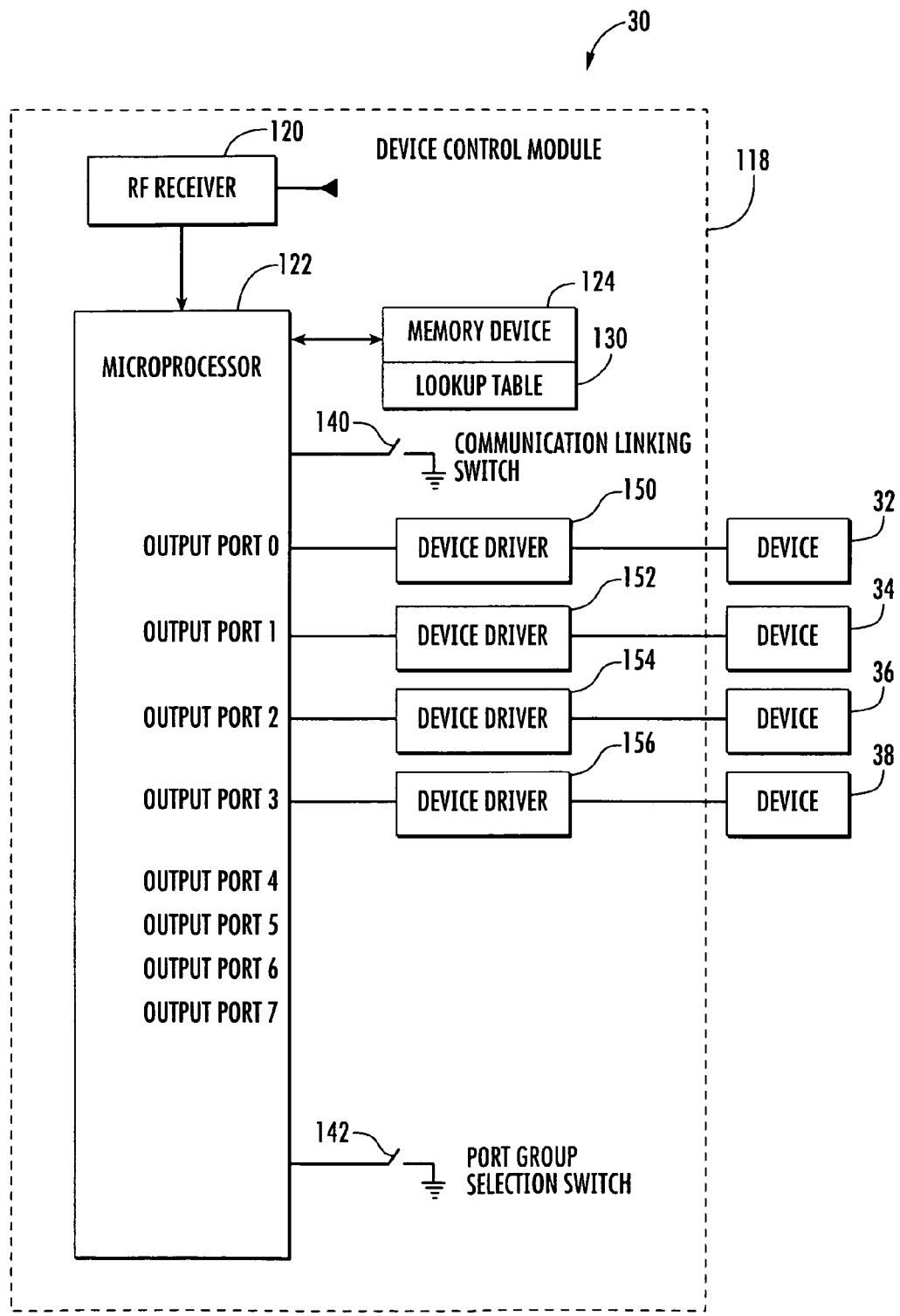
FIG. 3 is a block diagram of the device control module utilized in the system of FIG. 1.
Figure 8:
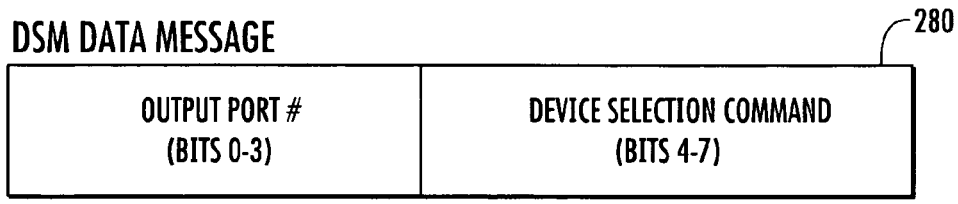
FIG. 8 is a schematic of another data message in another modulated RF signal transmitted by the device selection module of FIG. 2.

Thereafter, referring to FIGS. 2, 3 and 8, the microprocessor 62 generates another control signal to induce the RF transmitter 61 to transmit another modulated RF signal at the jump-to RF frequency (e.g., 900 MHz) having a data message 280 therein to be received by the DCM 30. The data message 280 has: (i) an output port number at bit positions 0-3 corresponding to both a device selection switch that was depressed on the DSM 20 and an associated output port of the DCM 30 to be controlled, and (ii) a device selection command at bit positions 4-7 indicating that one of the output ports of the DCM 30 is being selected by the DSM 20. For example, if the user depresses the device selection switch 80 in a closed operational position, the output port number "0000" corresponding to output port 0 of the DCM 30 would be in the data message 280. Alternately, if the user depresses the device selection switch 82, the output port number "0001" corresponding to output port 1 of the DCM 30 would be in the message 280.

After the communication linking operation between the DSM 20 and the DCM 30 has been completed, the microprocessor 62 monitors the device selection switches 80-94 to determine when a user depresses another one of the device selection switches 80-92 for selecting another output port of the DCM 30 coupled to a respective device to be controlled. For example, the microprocessor 62 monitors the device selection switches 80, 82, 84, 86 to determine when the user depresses another one of the device selection switches 80, 82, 84, 86 to select one of the output ports 0, 1, 2, 3 coupled to the devices 32, 34, 36, 38, respectively, to be controlled.

In one exemplary embodiment, the RF transmitter 61 can generate a modulated RF signal by modulating an RF signal containing a data message using a frequency shift keying (FSK) modulation technique. In an alternate embodiment, the RF transmitter 61 can generate a modulated RF signal by modulating an RF signal containing a data message using any other known modulation technique, such as amplitude modulation (AM), frequency modulation (FM), and amplitude shift keying (ASK), or the like.

Referring to FIGS. 1 and 3, the DCM 30 is provided to receive modulated RF signals from the DSM 20 and the FPMM 50 and to control one of the devices 32, 34, 36, 38 in response to the modulated RF signals. In particular, the DCM 30 receives modulated RF signals from the DSM 20 to determine which output port of the DCM 30 is being selected, which also selects the corresponding device coupled to the selected output port. Thereafter, the DCM 30 receives a modulated RF signals from the FPMM instructing the DCM 30 to either activate the selected output port (and corresponding device) or de-activate the selected output port (and corresponding device). The DCM 30 includes a housing 118, an RF receiver 120, a microprocessor 122, a memory device 124 having a lookup table 130 therein, a communication linking switch 140, a port group selection switch 142, and device drivers 150, 152, 154, 156. The microprocessor 122, the RF receiver 120, and the memory device 124 can be electrically powered utilizing a wall cube (not shown).

The housing 118 holds the RF receiver 120, the microprocessor 122, and the memory device 124 therein. The communication linking switch 140, the port group selection switch 142, and the device drivers 150, 152, 154, 156 extend at least partially through the housing 118 and are readily accessible by a user.

Referring to FIGS. 3 and 13, the microprocessor 122 is operably coupled to the RF receiver 120, the memory device 124, the communication linking switch 140, the port group selection switch 142, and the device drivers 150, 152, 154, 156. In particular, the processor 122 has a first group of output ports 0, 1, 2, 3 and a second group of output ports 4, 5, 6, 7. The DCM 30 is configured to utilize only one of the first and second groups of output ports at a time, based on an operational position of the port group selection switch 142. For example, if the port group selection switch 142 has a closed operational position, the microprocessor 122 can select one of the ports 0, 1, 2, 3 for subsequent activation. Alternately, if the port group selection switch 142 has an open operational position, the microprocessor 122 can select one of the ports 4, 5, 6, 7 for subsequent activation. As illustrated, in one exemplary embodiment, the output ports 0, 1, 2, 3 are electrically coupled to the device drivers 150, 152, 154, 156, respectively. When an output port of the DCM 30 has a high logic value, a device driver coupled to the output port activates a device coupled to the device driver. Alternately, when an output port of the DCM 30 has a low logic value, a device driver coupled to the output port de-activates or maintains de-activation of a device coupled to the device driver.

Referring to FIGS. 3 and 13, the microprocessor 122 utilizes the lookup table 130 to determine an RF frequency to utilize to receive modulated RF signals from the DSM 20 and the FPMM 50. In one exemplary embodiment, the lookup table 130 has the following fields: (i) RF frequency identifier, and (ii) RF frequency value. In particular, the microprocessor 122 accesses the record 372 in the table 130 to determine an initial RF frequency to use for initially receiving modulated RF signals from the DSM 20. Thereafter, the microprocessor 122 utilizes an RF frequency identifier in a data message received from the DSM 20 to select one of the records 374, 376 to determine a jump-to frequency indicated by a RF frequency value in the selected record for subsequent long-term communication with the DSM 20 and the FPMM 50, as will be discussed in greater detail below. Although the exemplary lookup table 130 is illustrated with three records for purposes of simplicity, in an alternative embodiment, the lookup table 130 could have a plurality of additional records each having a distinct RF frequency identifier and RF frequency value.

When a user depresses the communication linking switch 140 to a closed operational position, the microprocessor 122 enters a communication linking mode for a predetermined linking time interval, such as 15 seconds for example, within which the DCM 30 either establishes a communication link with the DSM 20 or the microprocessor 122 turns off or enters a sleep mode. A communication link between the DSM 20 and the DCM 30 is established when the DSM 20 and the DCM 30 are utilizing an identical jump-to frequency for transmission and reception, respectively. In particular, when the user depresses the communication linking switch 140 to the closed operational position, the microprocessor 122 accesses a record in the table 130 in the memory device 124 to determine an initial RF frequency to utilize for initially receiving modulated RF signals from the DSM 20. For example, the microprocessor 122 accesses the record 372 in the table 130 to determine an initial RF frequency of 900 MHz for receiving modulated RF signals from the DSM 20.

Thereafter, the RF receiver 120 receives a modulated RF signal (shown in FIG. 7) having a data message 270 with the RF frequency identifier indicating a jump-to frequency for subsequent long-term communication with the DSM 20 and the communication linking command indicating that a communication linking operation with the DSM 20 is desired. In response, the microprocessor 122 compares the communication linking command to a predetermined communication linking command stored in the memory device 124. If the communication linking command corresponds to the predetermined stored communication linking command then the microprocessor 122 selects a RF frequency indicated by the RF frequency identifier for subsequent RF signal reception. For example, if the data message 270 has an RF frequency identifier of "0001", the microprocessor accesses the record 374 having the RF frequency identifier "0001" and retrieves the associated RF frequency value 905 MHz corresponding to the jump-to frequency for subsequent long-term communication with the DSM 20. Also, the microprocessor 122 generates a control signal to induce the RF receiver 120 to receive modulated RF signals at 905 MHz and to disregard RF signals at other RF frequencies.

Thereafter, referring to FIGS. 3 and 8, the RF receiver 120 receives another modulated RF signal at the jump-to RF frequency from the DSM 20 having the data message 280 within the predetermined linking time interval. The data message 280 includes a device selection command and an output port number. In response, the microprocessor 122 compares the device selection command to a predetermined device selection command stored in the memory device 124. If the device selection command corresponds to the predetermined device selection command then the microprocessor 122 selects an output port corresponding to the output port number in the data message 280 for subsequent activation. For example, if the data message 280 has an output port number "0000" corresponding to output port 0 of the microprocessor 122, the microprocessor 122 would select the output port 0 for subsequent activation.

Referring to FIGS. 1 and 4, the FPMM 50 is provided to monitor an operational position of the movable member 234 of the foot pedal apparatus 52. Further, the FPMM 50 can transmit a modulated RF signal when the user displaces the movable member 234 from the first operational position to a second operational position. The communication between the FPMM 50 and the DCM 30 is "wireless" communication thus eliminating a plurality of communication wires between the FPMM 50 and the DCM 30. The FPMM 50 includes a housing 198, an RF transmitter 200, a microprocessor 202, a memory device 204 having a lookup table 206, and rotary switches 220, 222. The microprocessor 202, the RF transmitter 200, and the memory device 204 can be electrically powered utilizing a wall cube (not shown).

The housing 198 holds the RF transmitter 200, the microprocessor 202, and the memory device 204 therein. The rotary switches 220, 222 extend at least partially through the housing 198 and are readily accessible by a user.

The microprocessor 202 is operably coupled to the RF transmitter 200, the memory device 204, the rotary switches 220, 222, and the pressure sensor 55. The operational position of the rotary switch 100 indicates an office address (0-15) associated with the FPMM 50. The operational position of the rotary switch 222 indicates a room address (0-15) associated with the FPMM 50. It should be noted that when the system 10 is utilized in a specific office and room, the office address and room address for the FPMM 50 and the office address and room address for DSM 20, respectively, are identical so that both modules can effectively communicate with the DCM 30.

Referring to FIGS. 4 and 12, the microprocessor 202 utilizes the lookup table 206 to determine an RF frequency to utilize when communicating with the DCM 30. In one exemplary embodiment, the lookup table 202 has the following fields: (i) office address, (ii) room address, (iii) RF frequency identifier, and (iv) RF frequency value. In particular, the microprocessor 202 utilizes the office address and room address indicated by the rotary switches 220, 222, respectively, to select one of the records 354, 356 to determine a jump-to frequency indicated by a RF frequency value in the selected record for subsequent long-term communication with the DCM 30. For example, if an operational position of the rotary switches 220, 222 indicate an office address "0001" and a room address "0001", respectively, the microprocessor 202 accesses the record 354 having the office address value "0001" and the room address value "0001" to determine both the RF frequency identifier "0001", and the RF frequency value of 905 MHz indicating the jump-to RF frequency that will be utilized by the FPMM 50 to communicate with the DCM 30. Although the exemplary lookup table 206 is illustrated with two records for purposes of simplicity, in an alternative embodiment, the lookup table 206 could have a plurality of additional records each having a distinct office address, room address, RF frequency identifier, and RF frequency value.

Figure 9:
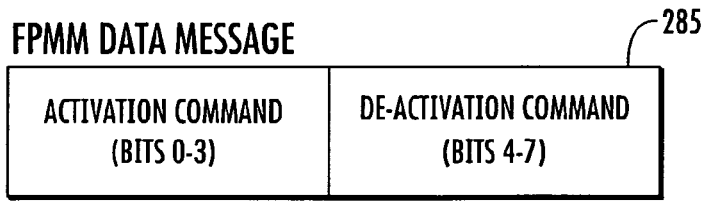
FIG. 9 is a schematic of a data message in a modulated RF signal transmitted by the foot pedal monitoring module of FIG. 4.

Referring to FIGS. 4 and 9, when the microprocessor 202 receives a signal from the pressure sensor 55 indicating that a user has at least partially displaced the moveable member 234 of the foot pedal apparatus 52 from a first operational position, the microprocessor 202 generates a control signal to induce the RF transmitter 200 to transmit a modulated RF signal at the jump-to RF frequency to be received by the DCM 30. The modulated RF signal has a data message 285 having an activation command. In one exemplary embodiment, the activation command is represented by binary value "111" at bit positions 0-3 in the data message 285.

Figure 10:
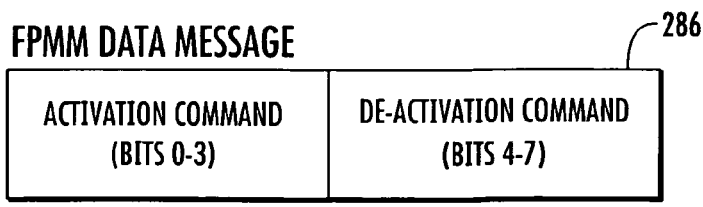
FIG. 10 is a schematic of another data message in another modulated RF signal transmitted by the foot pedal monitoring module of FIG. 4.
Figure 14:
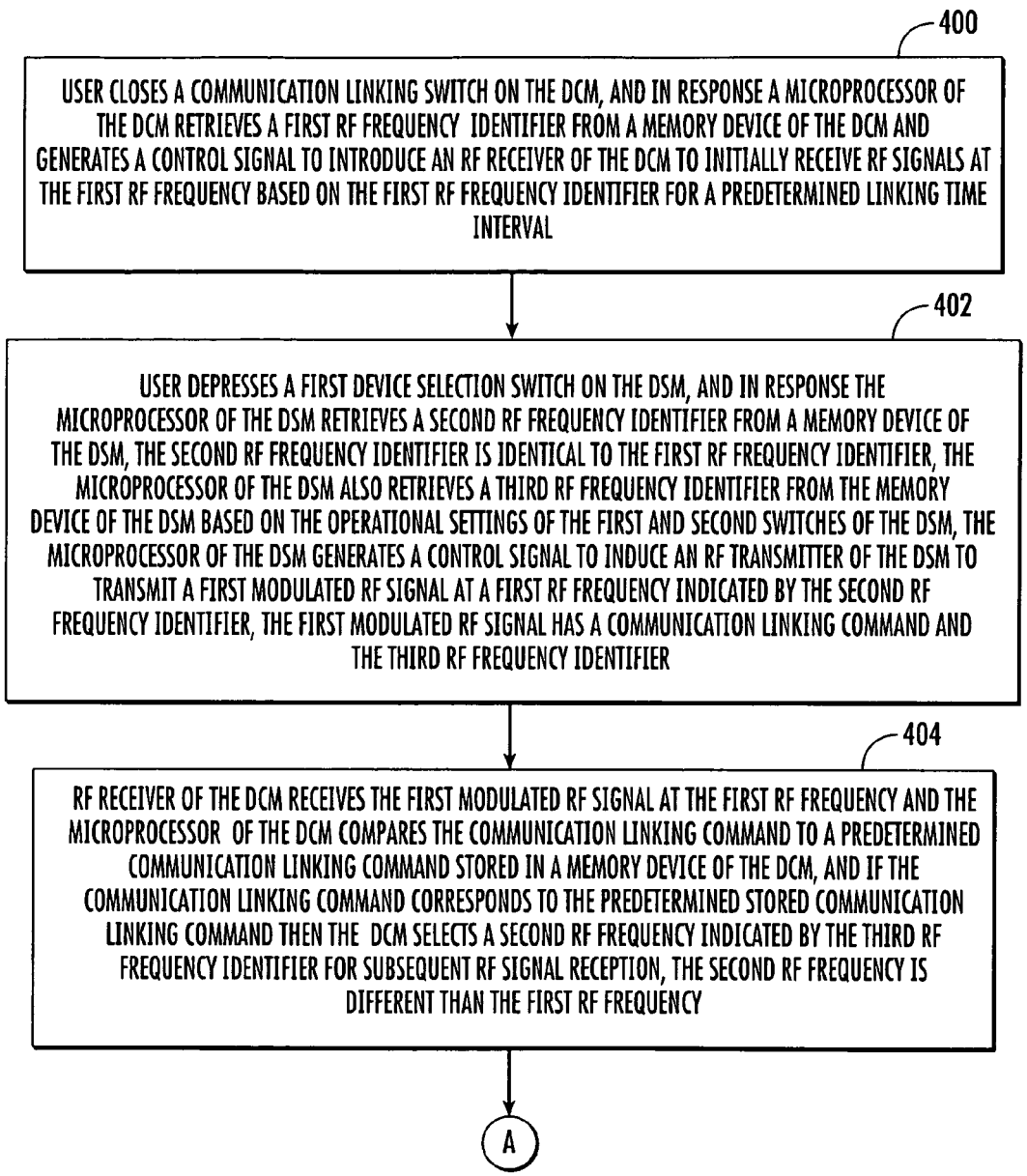
FIGS. 14-15 are flowcharts of a method for establishing a communication link between the device selection module of FIG. 2 and the device control module of FIG. 3 in accordance with another exemplary embodiment.
Figure 15:
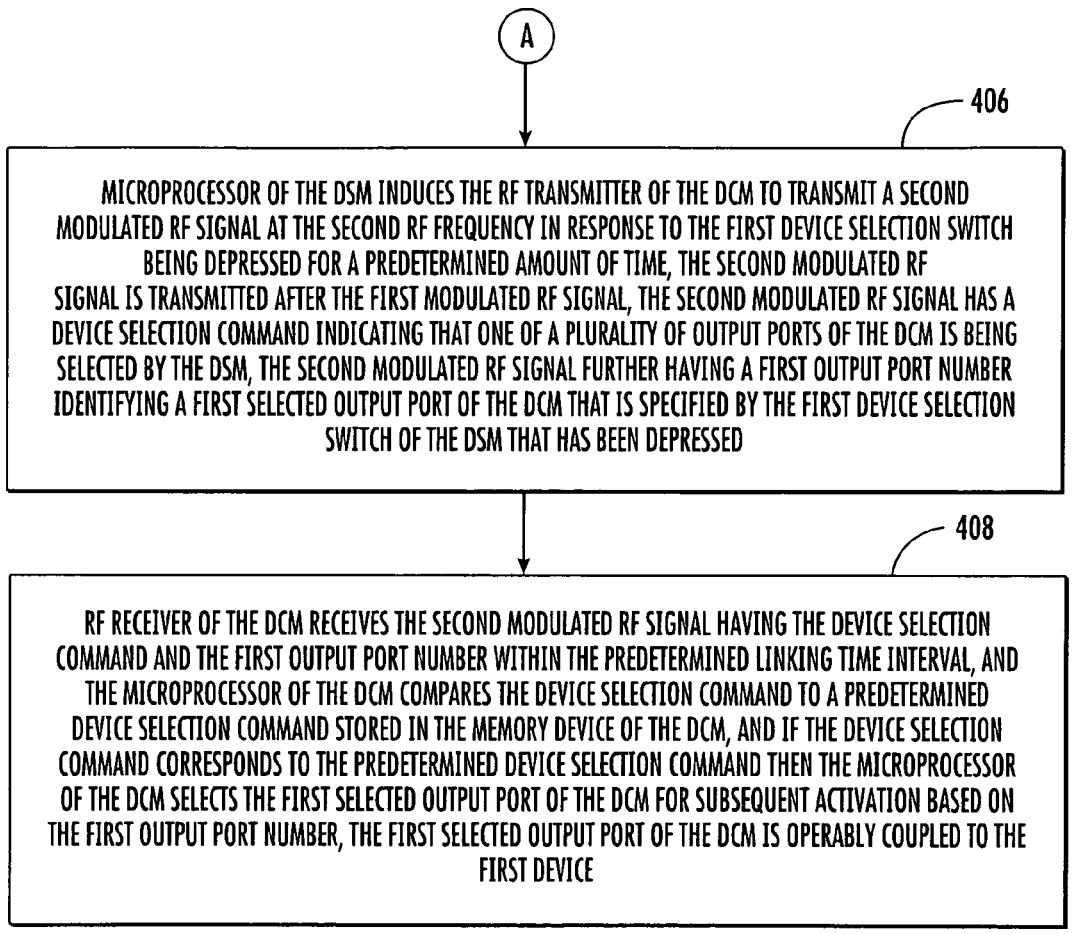
Figure 16:
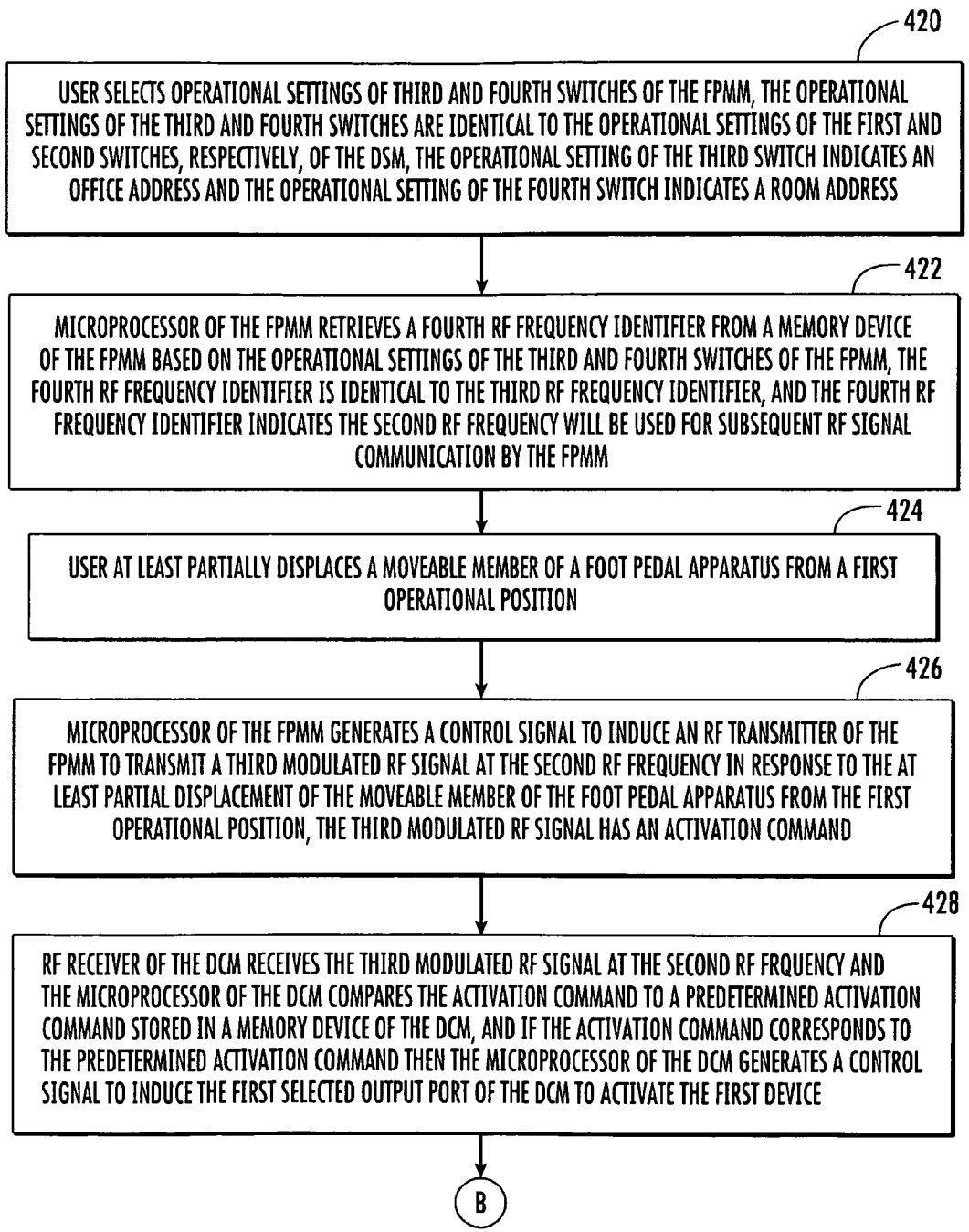
FIGS. 16-17 are flowcharts of a method for controlling a device coupled to the device control module of FIG. 3 utilizing the foot pedal monitoring module of FIG. 4 in accordance with another exemplary embodiment.
Figure 17:
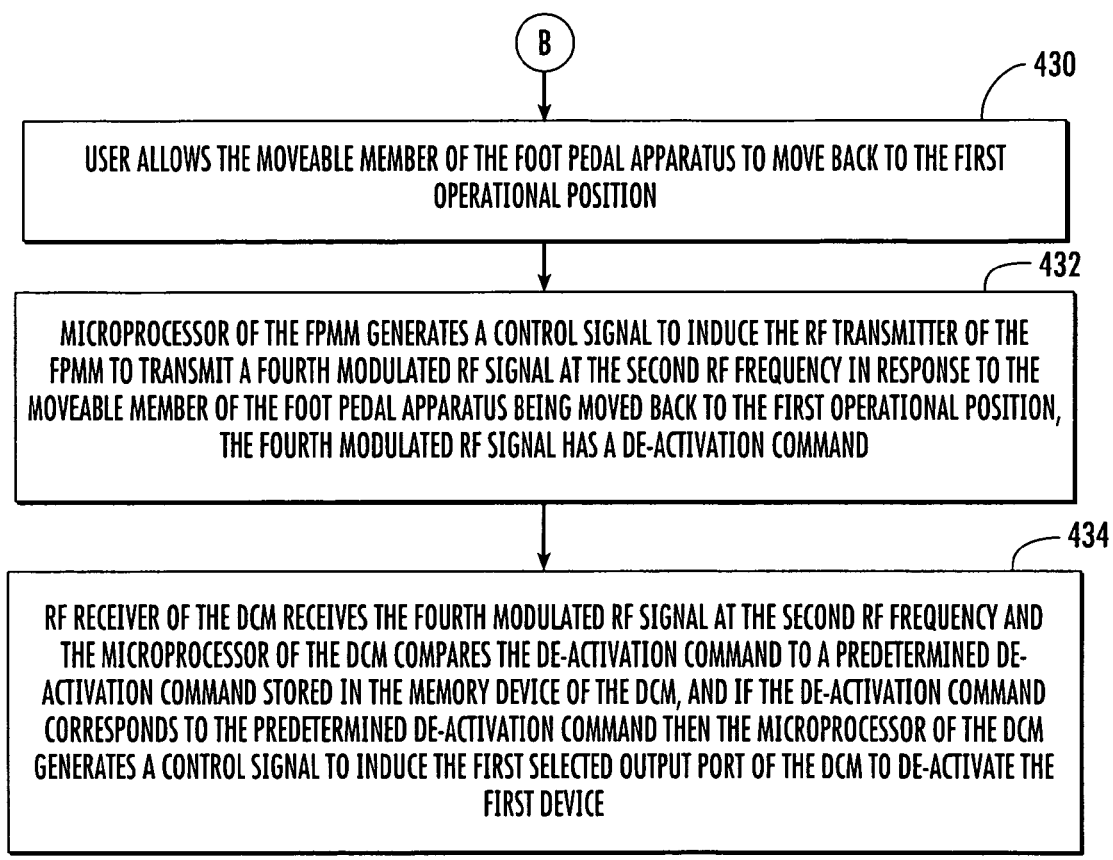

Alternately, referring to FIGS. 4 and 10, when the microprocessor 202 receives a signal from the pressure sensor 55 indicating that the user has allowed the moveable member 234 of the foot pedal apparatus 52 to move back to the first operational position, the microprocessor 202 generates another control signal to induce the RF transmitter 200 to transmit another modulated RF signal at the jump-to RF frequency to be received by the DCM 30. The modulated RF signal has a data message 286 having a de-activation command. In one exemplary embodiment, the de-activation command is represented by binary value "111" at bit positions 4-7 in the data message 286.

In one exemplary embodiment, the RF transmitter 200 can generate a modulated RF signal by modulating an RF signal containing a data message using a frequency shift keying (FSK) modulation technique. In an alternate embodiment, the RF transmitter 200 can generate a modulated RF signal by modulating an RF signal containing a data message using any other known modulation technique, such as amplitude modulation (AM), frequency modulation (FM), and amplitude shift keying (ASK), or the like.

Referring to FIG. 4, the foot pedal apparatus 52 is configured to allow a user to activate and de-activate devices utilizing a movable member 234. The foot pedal apparatus 52 includes a housing 230, the movable member 234, and a pneumatic valve 232. The foot pedal apparatus 52 is connected to an air source 53 utilizing a tube 58. The air source 53 supplies pressurized air at a predetermined pressure through the tube 58 to the pneumatic valve 232. The pneumatic valve 232 is further operatively coupled to the tube 59 which extends from the pneumatic valve 232 to the pneumatic valve 56. Also, a pressure sensor 55 is operatively coupled to the tube 59. The pressure sensor 55 generates a signal indicating a pressure level in the tube 59 which is further indicative of whether the moveable member 234 is depressed or not depressed, that is received by the microprocessor 202.

Referring to FIGS. 4 and 9, when a foot 236 of a user displaces the movable member 234 from a first operational position, the pneumatic valve 232 opens to propagate pressurized air from the air source 53 to the pneumatic bleed-off valve 56. Also, the pressure sensor 55 generates a pressure signal indicative of the pressure in the tube 59. When the pressure signal indicates an air pressure level greater than or equal to the threshold pressure level when the movable member 234 is moved from the first operational position to a second operational position, the microprocessor 202 generates a control signal to induce the RF transmitter 200 to transmit a modulated RF signal at the jump-to frequency having the data message 285 with an activation command to induce the DCM 30 to turn on the selected device.

Alternately, referring to FIGS. 4 and 10, when the pressure signal indicates an air pressure level less than the threshold pressure level when the movable member 234 returns to the first operational position, the microprocessor 202 generates a control signal to induce the RF transmitter 200 to transmit a modulated RF signal at the jump-to frequency having the data message 286 with a de-activation command to induce the DCM 30 to turn off the selected device.

Figure 5:
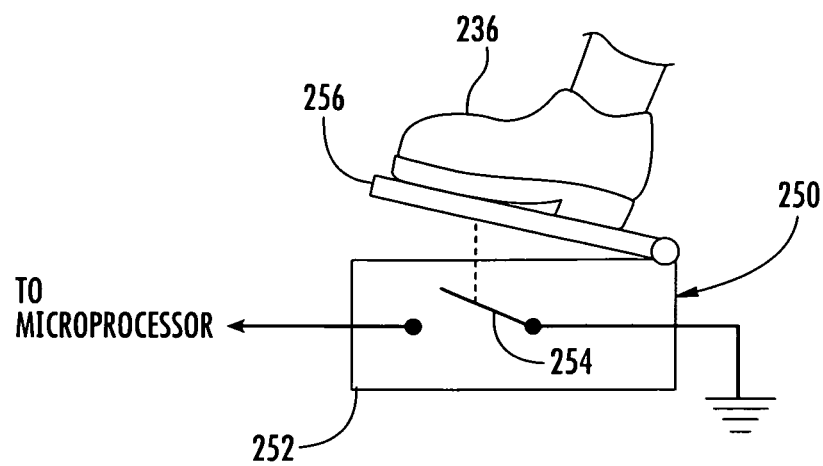
FIG. 5 is a schematic of an alternative foot pedal apparatus having a first operational position that can be utilized in the system of FIG. 1.
Figure 6:
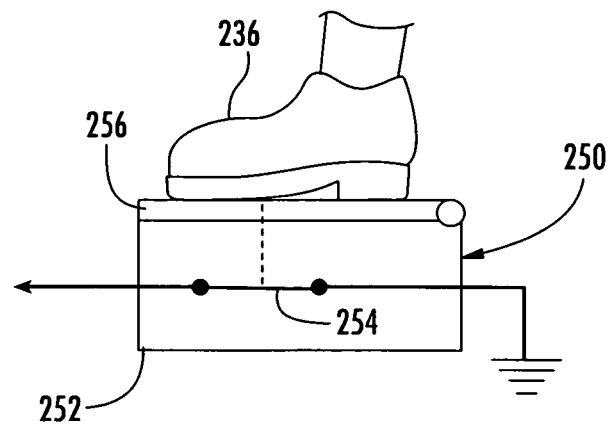
FIG. 6 is a schematic of the foot pedal apparatus of FIG. 5 having a second operational position.

Referring to FIGS. 4, 5 and 6, in an alternate embodiment, the foot pedal apparatus 52, the air source 53, the pressure sensor 55, the valve 56, and the tubes 58, 59 can be replaced with a foot pedal apparatus 250. The foot pedal apparatus 250 includes a housing 252, an electrical switch 251, and a movable member 256. The electrical switch 254 is electrically coupled between electrical ground and the microprocessor 202. The movable member 256 is also operably coupled to the electrical switch 252. When the user's foot 236 pivots the movable member 256 from a first operational position (shown in FIG. 5) to a second operational position (shown in FIG. 6), the switch 251 is moved from an open operational position to a closed operational position, respectively. Thereafter, the microprocessor 202 detects a ground voltage signal associated with the foot pedal apparatus 52. In response to the ground voltage signal, the microprocessor 202 generates a control signal for inducing the RF transmitter 78 to transmit a modulated RF signal at the jump-to frequency having the data message 285 with an activation command to induce the DCM 30 to turn on the selected device. Also, when the movable member 234 returns to the first operational position which induces the switch 251 to move from the closed operational position to the open operational position, the microprocessor 202 generates a control signal to induce the RF transmitter 200 to transmit a modulated RF signal at the jump-to frequency having the data message 286 with a de-activation command to induce the DCM 30 to turn off the selected device.

Referring to FIG. 1, the devices 32, 34, 26, 38 may comprise any electrically, pneumatically, magnetically, or hydraulically actuated device. For example, devices 32, 34, 26, 38 may comprise electrically, pneumatically, magnetically, or hydraulically actuated medical or dental devices. Further, the devices 32, 34, 26, 38 may comprise one or more of the following devices: a drill, a dental chair whose chair position can be adjusted automatically, an infrared photo-optic imaging camera, a dental irrigator, an intra-oral camera, a laser, an air-abrasion unit, an electro-surgery unit, an ultrasonic teeth cleaning unit, a piezo-ultrasonic unit, an air polishing prophylaxis device, a gum depth measurement probe, a surgical microscope, a microprocessor controlled anesthetic delivery system, and an endodontic heat source device.

For example, one or more of the devices 32, 34, 26, 38 can comprise a torque control motor drill sold under the trademark Tecnika and is manufactured by Advanced Technology Research (ATR), located at Via del Pescino, 6, 51100 Pistoia, Italy, and sold in the United States by Dentsply Tulsa Dental at 5001 E. 68$^{th}$, Tulsa, Okla. 74136-3332. Further, it should be noted that the DCM 30 could be used to control operation of any electrically controlled or pneumatically controlled drill.

Further, for example, one or more of the devices 32, 34, 26, 38 can comprise a dental chair sold under the trademark Priority manufactured by A-DEC located at 2601 Crestview Drive, Newberg, Oreg., which provides elevational control of the chair, tilting of the back of the chair, and memory recall positions. Thus, the elevation position, tilting position, and other variable position adjustments could be controlled by the system 10. Further, it should be noted that the DCM 30 could be used to control operation of any electrically controlled or hydraulically controlled dental chair or control unit associated with the dental chair.

Also, for example, one or more of the devices 32, 34, 26, 38 can comprise an infrared photo-optic imaging camera sold under the trademark CEREC® manufactured by Sirona Dental Systems located at Fabrikstrabe 31, 64625 Bensheim, Hessen, Germany, and sold in the United States by Patterson Dental Supply, Inc., located at 1031 Mendota Heights Rd., Saint Paul, Minn. 55120. Further, it should be noted that the DCM 30 could be used to control any imaging camera that can be automatically or externally controlled to generate a digital image or a film image.

Still further, for example, one or more of the devices 32, 34, 26, 38 can comprise a dental irrigator sold under the trademark Piezon® Master 600, manufactured by Electro Medical Systems located at 12092 Forestgate Drive, Dallas Tex., 75243. Further, it should be noted that the DCM 30 could be used to control operation of any dental irrigator or dental irrigator control system that directs fluid under pressure therethrough.

Also, for example, one or more of the devices 32, 34, 26, 38 can comprise an intra-oral camera sold under the trademark Prism™, manufactured by Professional Dental Technologies, Inc., located at 2410 Harrison Street, Batesville, Ark. 72501, or the AcuCam Concept IV manufactured by Gendex, a division of Dentsply International located at 901 W. Oakton St., Des Plains, Ill. 60018-1884. Further, it should be noted that the DCM 30 could be used to control operation of any intra-oral camera (or video capture card or video capture computer associated with the camera) to generate, store, retrieve, display, or print a digital or analog video image.

In addition, for example, one or more of the devices 32, 34, 26, 38 can comprise a laser sold under the trademark Odyssey™, manufactured by Ivoclar Vivadent Inc., located at 175 Pineview Drive, Amherst, N.Y. 14228. Alternately, the system 10 could be utilized with a laser sold under the trademark Waterlase®, manufactured by Biolase Technology, Inc., located at 981 Calle Amanecer, San Clemente, Calif. 92673. Further, it should be noted that the DCM 30 could be used to control operation of any other known laser.

Further, for example, one or more of the devices 32, 34, 26, 38 can comprise an air-abrasion unit sold under the trademark PrepStart™, manufactured by Danville Engineering, located at 2021 Omega Road, San Ramon Calif. 94583. Further, it should be noted that the DCM 30 could be used to control operation of any other type of air-abrasion unit utilized in dental procedures, in medical procedures, or during processing or cleaning of manufactured goods.

Also, for example, one or more of the devices 32, 34, 26, 38 can comprise an electro-surgery unit sold under the trademark Hyfrecator® 2000, manufactured by ConMed® Corporation, located at 310 Broad Street, Utica, N.Y. 13501. Further, it should be noted that the DCM 30 could be used to control operation of any other electro-surgery unit that utilizes electrical energy for removing tissue or bone.

Further, for example, one or more of the devices 32, 34, 26, 38 can comprise the ultrasonic teeth cleaning unit sold under the trademark Cavitron 3000 manufactured by Dentsply International located at 901 W. Oakton Street, Des Plains, Ill. 60018-1884. Further, it should be noted that the DCM 30 could be used to control operation of any other ultrasonic teeth cleaning unit.

Still further, for example, one or more of the devices 32, 34, 26, 38 can comprise a piezo-ultrasonic unit sold under the trademark Spartan MTS™, manufactured by Obtura Spartan located at 1663 Fenton Business Park Court, Fenton, Missouri 63026. Further, it should be noted that the DCM 30 could be used to control operation of any other piezo-ultrasonic unit that agitates or vibrates a tip for cleaning teeth or removing tooth structure. Piezo-ultrasonic units may have fluid cooled tips.

Further, for example, one or more of the devices 32, 34, 26, 38 can comprise an air polishing prophylaxis device sold under the trademark Cavitron Prophy-Jet®, manufactured by Dentsply International located at 901 W. Oakton Street, Des Plains, Ill. 60018-1884. Further, it should be noted that the DCM 30 could be used to control operation of any other air polishing prophylaxis device that uses compressed air for delivering a fluid and/or an abrasive compound out of a nozzle for cleaning teeth and gums.

In addition, for example, one or more of the devices 32, 34, 26, 38 can comprise the gum depth measurement probe sold under the trademark Florida Probe®, manufactured by Florida Probe Corporation, located at 3700 NW 91$^{st}$ Street, Suite C-100, Gainesville, Fla. 32606. Further, it should be noted that the DCM 30 could be used to control operation of any other gum depth measurement probe that can be automatically or externally controlled to take a gum depth measurement.

Further, for example, one or more of the devices 32, 34, 26, 38 can comprise a surgical microscope sold under the trademark Protégé™, manufactured by Global Surgical Corporation, located at 3610 Tree Court Industrial Blvd., St. Louis, Mo. 63122-6622. Further, it should be noted that the DCM 30 could be used to control operation of any other surgical microscope that includes one or more of: automatically controllable height adjustment, automatically controllable focusing, automatically controllable field of view size, viewing lights, and a camera associated with the surgical microscope.

Further, for example, one or more of the devices 32, 34, 26, 38 can comprise an anesthetic delivery system sold under the trademark The Wand™ II, manufactured by the Dental Division of Milestone Scientific located at 151 S. Pfingsten Road, Deerfield, Ill. 60015. Further, it should be noted that the DCM 30 could be used to control operation of any other microprocessor-controlled anesthetic delivery system that delivers predetermined amounts of an anesthetic to a medical or dental patient.

Further, for example, one or more of the devices 32, 34, 26, 38 can comprise an endodontic heat source device sold under the trademark System B HeatSource™ model 1005, manufactured by Analytic-Sybron Dental Specialties located at 1332 South Lone Hill Avenue, Glendora, Calif. 91740. Further, it should be noted that the DCM 30 could be used to control operation of any other endodontic heat source device.

Further, for example, one or more of the devices 32, 34, 26, 38 can comprise a video capture circuit. The DCM 30 can receive a modulated RF signal and induce the video capture circuit to store a video image in an internal memory device in response to the modulated RF signal.

Referring to FIGS. 2, 3, 14 and 15, a flowchart of a method of establishing a communication link between the DSM 20 and the DCM 30 will now be explained.

At step 400, a user closes a communication linking switch 140 on the DCM 30, and in response the microprocessor 122 of the DCM 30 retrieves a first RF frequency identifier from the memory device 124 generates a control signal to induce the RF receiver 120 to initially receive RF signals at the first RF frequency based on the first RF frequency identifier for a predetermined linking time interval.

At step 402, the user depresses a first device selection switch 80 on the DSM 20, and in response the microprocessor 62 retrieves a second RF frequency identifier from the memory device 64. The second RF frequency identifier is identical to the first RF frequency identifier. Also, the microprocessor 62 retrieves a third RF frequency identifier from the memory device 64 based on the operational settings of the rotary switches 100, 102. Further, the microprocessor 62 generates a control signal to induce the RF transmitter 61 of the DSM 20 to transmit a first modulated RF signal at a first RF frequency indicated by the second RF frequency identifier. The first modulated RF signal has a data message with a communication linking command, and the third RF frequency identifier indicates the jump-to frequency.

At step 404, the RF receiver 120 of the DCM 30 receives the first modulated RF signal at the first RF frequency and the microprocessor 122 compares the communication linking command to a predetermined communication linking command stored in the memory device 124. If the communication linking command corresponds to the predetermined stored communication linking command then the microprocessor 122 selects a second RF frequency (i.e., jump-to frequency) indicated by the third RF frequency identifier for subsequent RF signal reception. The second RF frequency is different than the first RF frequency.

At step 406, the microprocessor 62 of the DSM 20 induces the RF transmitter 61 to transmit a second modulated RF signal at the second RF frequency in response to the first device selection switch 80 being depressed by a user for a predetermined amount of time. The second modulated RF signal is transmitted after the first modulated RF signal. The second modulated RF signal has a data message with a device selection command indicating one of a plurality of output ports of the DCM 30 is being selected by the DSM 20. The data message in the second modulated RF signal further includes a first output port number identifying a first selected output port of the DCM 30, that is specified by the first device selection switch 80 being depressed or operationally closed by the user.

At step 408, the RF receiver 120 of the DCM 30 receives the second modulated RF signal having data message with the device selection command and the first output port number within the predetermined linking time interval. In response, the microprocessor 122 compares the device selection command to a predetermined device selection command stored in the memory device 124. If the device selection command corresponds to the predetermined device selection command then the microprocessor 122 selects the first selected output port of the DCM 30 for subsequent activation based on the first output port number. The first selected output port is operably coupled to the device 32.

Referring to FIGS. 3, 4, 16 and 17, a flowchart of a method for controlling the DCM 30 utilizing the FPMM 30 will now be explained.

At step 420, a user selects operational settings of third and fourth switches 220, 222 of the FPMM 50. The operational settings of the third and fourth switches 220, 222 are identical to the operational settings of the first and second switches 100, 102, respectively, of the DSM 20. The operational setting of the third switch 220 indicates an office address and the operational setting of the fourth switch 22 indicates a room address.

At step 422, the microprocessor 202 of the FPMM 50 retrieves a fourth RF frequency identifier from the memory device 204 based on the operational settings of the third and fourth switches 220, 222. The fourth RF frequency identifier is identical to the third RF frequency identifier. The fourth RF frequency identifier indicates the second RF frequency will be used for subsequent RF signal communication by the FPMM 50.

At step 424, the user at least partially displaces the moveable member 234 of the foot pedal apparatus 52 from a first operational position.

At step 426, the microprocessor of the FPMM 50 generates a control signal to induce the RF transmitter 200 to transmit a third modulated RF signal at the second RF frequency in response to the at least partial displacement of the moveable member 234 of the foot pedal apparatus 52 from the first operational position. The third modulated RF signal has a data message with an activation command.

At step 428, the RF receiver 120 of the DCM 30 receives the third modulated RF signal at the second RF frequency and the microprocessor 122 compares the activation command to a predetermined activation command stored in the memory device 124. If the activation command corresponds to the predetermined activation command then the microprocessor 122 generates a control signal to induce the first selected output port of the DCM 30 to activate the device 32, using the device driver 150.

At step 430, the user allows the moveable member 234 of the foot pedal apparatus 52 to move back to the first operational position.

At step 432, the microprocessor of the FPMM 50 generates a control signal to induce the RF transmitter 200 to transmit a fourth modulated RF signal at the second RF frequency in response to the moveable member 234 of the foot pedal apparatus 52 being moved back to the first operational position. The fourth modulated RF signal has data message with a de-activation command.

At step 434, the RF receiver 129 of the DCM 30 receives the fourth modulated RF signal at the second RF frequency and the microprocessor 122 compares the de-activation command to a predetermined de-activation command stored in the memory device 124 of the DCM 30. If the de-activation command corresponds to the predetermined de-activation command then the microprocessor 122 generates a control signal to induce the first selected output port of the DCM 30 to de-activate the device 80, using the device driver 150.

Figure 18:
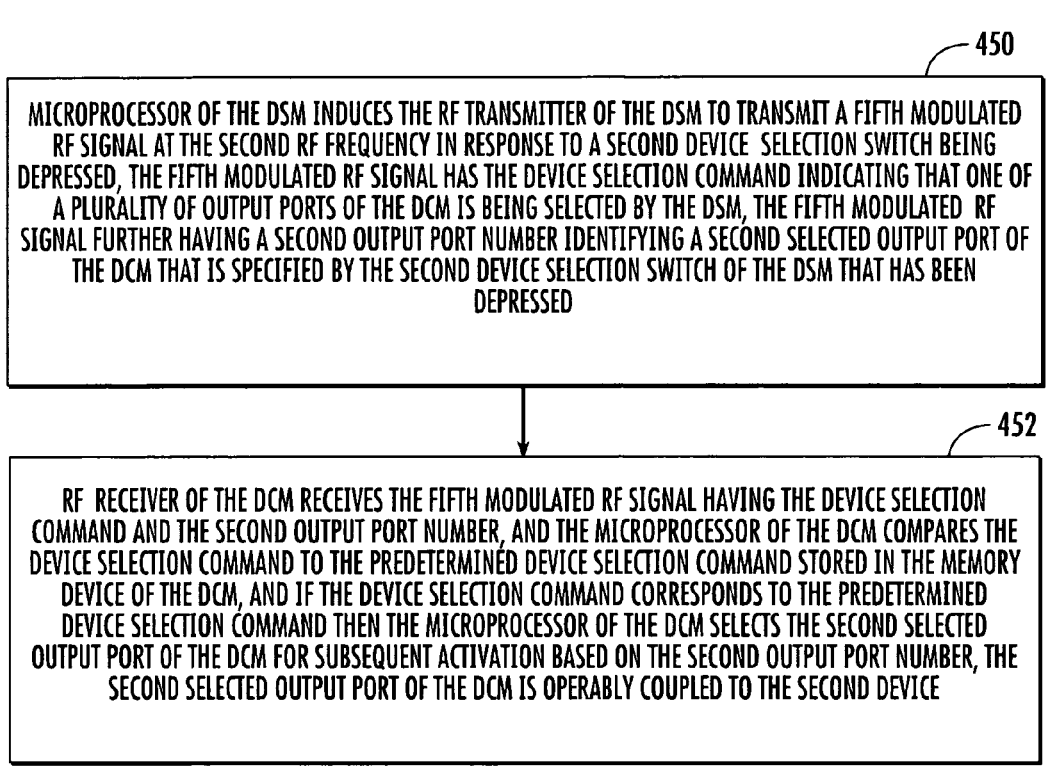
FIG. 18 is a flowchart of a method for selecting a device to be controlled by the device control module of FIG. 3 utilizing the device selection module of FIG. 2 in accordance with another exemplary embodiment.

Referring to FIGS. 2, 3 and 18, a flowchart of a method for selecting a second device to be controlled by the DCM 30 utilizing the DSM 20 will now be explained.

At step 450, the microprocessor 62 of the DSM 20 induces the RF transmitter 62 to transmit a fifth modulated RF signal at the second RF frequency in response to a second device selection switch 82 being depressed by a user. The fifth modulated RF signal has data message with the device selection command indicating that one of a plurality of output ports of the DCM 30 is being selected by the DSM 20. The data message in the fifth modulated RF signal further includes a second output port number identifying a second selected output port of the DCM 30 that is specified by the second device selection switch 82 of the DSM 20 being depressed.

At step 452, the RF receiver 120 of the DCM 30 receives the fifth modulated RF signal having the data message with the device selection command and the second output port number. The microprocessor 122 of the DCM 30 compares the device selection command to the predetermined device selection command stored in the memory device 124 of the DCM 30. If the device selection command corresponds to the predetermined device selection command then the microprocessor 122 selects the second selected output port of the DCM 30 for subsequent activation, by the FPMM 50, based on the second output port number. The second selected output port of the DCM 30 is operably coupled to the device 34 via the device driver 152.

The inventive system and method for remotely controlling at least one device provides a substantial advantage over other systems and methods. In particular, the system and method provide a technical effect of initially establishing a communication link between the DSM and the DCM by transmitting a first RF signal at a first frequency having an RF identifier to specify a jump-to frequency, and then transmitting a second RF signal at the jump-to frequency specifying an output port number that is to be selected, within predetermined linking time interval. As a result, the DCM can be easily linked to the DSM for selecting devices to be controlled.

While the invention is described with reference to the exemplary embodiments, it will be understood by those skilled in the art that various changes may be made and equivalent elements may be substituted for elements thereof without departing from the scope of the invention. In addition, many modifications may be made to the teachings of the invention to adapt to a particular situation without departing from the scope thereof. Therefore, is intended that the invention not be limited the embodiments disclosed for carrying out this invention, but that the invention includes all embodiments falling with the scope of the intended claims. The use of the term's first, second, etc. does not denote any order of importance, but rather the term's first, second, etc. are to distinguish one element from another.

What is claimed is:

1. A system for remotely controlling at least a first device based on operation of a foot pedal apparatus, the foot pedal apparatus having a movable member, comprising:
    a device selection module configured to transmit a first modulated RF signal at a first RF frequency having a communication linking command and a first RF frequency identifier, the first RF frequency identifier indicating a second RF frequency different than the first RF frequency;
    a device control module configured to receive the first modulated RF signal at the first RF frequency and to compare the communication linking command to a predetermined communication linking command, if the communication linking command corresponds to the predetermined communication linking command then the device control module selects the second RF frequency based on the first RF frequency identifier for subsequent RF signal reception;
    a foot pedal monitoring module configured to transmit a second modulated RF signal at the second RF frequency in response to at least partial displacement of the moveable member of the foot pedal apparatus from a first operational position; and
    the device control module further configured to receive the second modulated RF signal at the second RF frequency and to control operation of the first device in response to the second modulated RF signal.

2. The system of claim 1, wherein the device selection module is further configured to transmit a third modulated RF signal, the third modulated RF signal being transmitted after the first modulated RF signal and before the second modulated RF signal, the third modulated RF signal having a device selection command indicating that one of a plurality of output ports of the device control module is being selected by the device selection module, the third modulated RF signal further having an output port number identifying a selected output port of the device control module, the predetermined output port being operably coupled to the first device, the third modulated RF signal being transmitted in response to a device selection switch of the device selection module being depressed.

3. The system of claim 1, wherein the device selection module has a hand-held housing, a first microprocessor, a first memory device, and first and second switches; the first memory device and the first and second switches being operably coupled to the first microprocessor; the first microprocessor configured to retrieve the first RF frequency identifier from the first memory device based on operational settings of the first and second switches.

4. The system of claim 3, wherein the first switch has a first operational setting indicating an office address, and the second switch has a second operational setting indicating a room address.

5. The system of claim 3, wherein the foot pedal monitoring module has a second microprocessor, a second memory device, and third and fourth switches; the second memory device and the third and fourth switches being operably coupled to the second microprocessor; the second microprocessor configured to retrieve a second RF frequency identifier from the second memory device based on operational settings of the third and fourth switches, the second RF frequency identifier being identical to the first RF frequency identifier, the second RF frequency identifier indicating the second RF frequency.

6. The system of claim 1, wherein the foot pedal monitoring module is further configured to detect the at least partial displacement of the moveable member of the foot pedal apparatus by monitoring a pressure level in a tube operably coupled to the foot pedal apparatus.

7. The system of claim 1, wherein the foot pedal monitoring module is further configured to detect the at least partial displacement of the moveable member of the foot pedal apparatus by monitoring an operational state of an electric switch operably coupled to the moveable member.

8. The system of claim 1, wherein the second modulated RF signal further includes an activation command, the device control module configured to receive the second modulated RF signal and to activate the first device in response to the activation command.

9. The system of claim 8, wherein the foot pedal monitoring module is further configured to transmit a third modulated RF signal having a de-activation command after transmitting the second modulated RF signal when the moveable member is returned to the first operational position, the device control module further configured to receive the third modulated RF signal and to de-activate the first device in response to the de-activation command.

10. The system of claim 9, wherein the device control module is configured to maintain activation of the first device during a first time period from at least receipt of the second modulated RF signal to receipt of the third modulated RF signal.

11. The system of claim 1, wherein the first device comprises a dental implement or a medical implement.

12. The system of claim 1, wherein the first device comprises one of a drill, a microprocessor position-controllable dental chair, an infrared photo-optic imaging camera, a dental irrigator, an intra-oral camera, a video capture circuit, a laser, an air-abrasion unit, an electro-surgery unit, an ultrasonic teeth cleaning unit, a piezo-ultrasonic unit, an air polishing prophylaxis device, a gum depth measurement probe, a surgical microscope with controllable focusing adjustment, a microprocessor controlled anesthetic delivery system, and an endodontic heat source device.

13. The system of claim 1, wherein the first device comprises a video capture circuit, the device control module operably coupled to the video capture circuit, the device control module configured to receive the second modulated RF signal and to induce the video capture circuit to store a video image in an memory device in response to the second modulated RF signal.

14. A method for remotely controlling at least a first device based on operation of a foot pedal apparatus having a movable member, comprising:

transmitting a first modulated RF signal at a first RF frequency having a communication linking command and a first RF frequency identifier utilizing a device selection module, the first RF frequency identifier indicating a second RF frequency different than the first RF frequency;

receiving the first modulated RF signal at the first RF frequency at a device control module and comparing the communication linking command to a predetermined communication linking command utilizing the device control module;

if the communication linking command corresponds to the predetermined communication linking command then selecting the second RF frequency based on the first RF frequency identifier utilizing the device control module for subsequent RF signal reception by the device control module;

transmitting a second modulated RF signal at the second RF frequency from a foot pedal monitoring module in response to at least partial displacement of the moveable member of the foot pedal apparatus from a first operational position; and receiving the second modulated RF signal at the second RF frequency at the device control module and controlling operation of the first device in response to the second modulated RF signal utilizing the device control module.

15. The method of claim 14, further comprising:

determining if a device selection switch of the device selection module has been depressed;

if the device selection switch has been depressed, then transmitting a third modulated RF signal having a device selection command indicating that one of a plurality of output ports of the device control module is being selected by the device selection module, the third modulated RF signal further having an output port number identifying a selected output port of the device control module, the selected output port being operably coupled to the first device, the third modulated RF signal being transmitted after the first modulated RF signal and before the second modulated RF signal.

16. The method of claim 14, wherein the second modulated RF signal further includes an activation command, the method further comprising receiving the second modulated RF signal at the device control module and activating the first device in response to the activation command utilizing the device control module.

17. The method of claim 16, further comprising:

transmitting a third modulated RF signal having a de-activation command utilizing the foot pedal monitoring module after transmitting the second modulated RF signal when the moveable member is at the first operational position; and receiving the third modulated RF signal at the device control module and de-activating the first device in response to the de-activation command utilizing the device control module.

18. The method of claim 17, further comprising maintaining activation of the first device during a first time period from at least receipt of the second modulated RF signal to receipt of the third modulated RF signal utilizing the device control module.

* * * * *